(12) United States Patent
Tsukii et al.

(10) Patent No.: US 8,482,723 B2
(45) Date of Patent: Jul. 9, 2013

(54) OPTICAL INFORMATION ANALYZER AND OPTICAL INFORMATION ANALYSIS METHOD

(75) Inventors: Ken Tsukii, Tokyo (JP); Kenichi Kimura, Tokyo (JP); Toru Takahashi, Tokyo (JP); Jie Xu, Tokyo (JP)

(73) Assignee: Furukawa Electric Co., Ltd., Tokyo (JP)

( * ) Notice: Subject to any disclaimer, the term of this patent is extended or adjusted under 35 U.S.C. 154(b) by 0 days.

(21) Appl. No.: 13/337,848

(22) Filed: Dec. 27, 2011

(65) Prior Publication Data

US 2012/0154804 A1 Jun. 21, 2012

Related U.S. Application Data

(63) Continuation of application No. PCT/JP2010/055811, filed on Mar. 31, 2010.

(51) Int. Cl.
  *G01N 21/00* (2006.01)
(52) U.S. Cl.
  USPC .......................................................... 356/73
(58) Field of Classification Search
  USPC ...................................... 356/72–73
  See application file for complete search history.

(56) References Cited

U.S. PATENT DOCUMENTS

| 5,730,941 | A | 3/1998 | Lefevre et al. |
| 7,443,491 | B2 * | 10/2008 | Kanda ............................. 356/73 |
| 7,957,002 | B2 | 6/2011 | Tsukii et al. |
| 8,149,402 | B2 * | 4/2012 | Rich et al. ...................... 356/343 |
| 2006/0152707 | A1 | 7/2006 | Kanda |
| 2010/0233753 | A1 | 9/2010 | Tsukii et al. |
| 2011/0199612 | A1 | 8/2011 | Tsukii et al. |

FOREIGN PATENT DOCUMENTS

| CN | 1153300 A | 7/1997 |
| CN | 101072997 A | 11/2007 |
| JP | 60-29643 | 2/1985 |
| JP | 5-10946 | 1/1993 |
| JP | 9-166541 | 6/1997 |
| JP | 3691925 B2 | 12/2006 |
| JP | 2008-292448 | 12/2008 |
| WO | WO 2005/017969 A2 | 2/2005 |

OTHER PUBLICATIONS

International Search Report issued Jul. 6, 2010, in PCT/JP2010/055811.

(Continued)

*Primary Examiner* — Tarifur Chowdhury
*Assistant Examiner* — Abdullahi Nur
(74) *Attorney, Agent, or Firm* — Oblon, Spivak, McClelland, Maier & Neustadt, L.L.P.

(57) ABSTRACT

An optical information analyzer (10) includes a light emitting unit (30) that emits light (excitation light) (L0) to a sample (S), a transmission light receiving unit (50) that receives transmission light (L1), which is the excitation light passing through the sample (S), and detects the received transmission light as a transmission light signal (SG1), scattered light/fluorescence receiving units (60) and (70) that are provided at a plurality of positions, receive side scattered light/fluorescence components (L2) and (L3) from the sample (S), and detect the received side scattered light/fluorescence components as scattered light/fluorescence signals (SG2) and (SG3), and an analyzing unit (90) that measures the optical information of the sample (S) on the basis of the detected scattered light/fluorescence signals (SG2) and (SG3) and the detected transmission light signal (SG1) and analyzes the sample (S) on the basis of the measured optical information.

21 Claims, 5 Drawing Sheets

OTHER PUBLICATIONS

Office Action issued Apr. 8, 2011, in Japanese Patent Application No. 2010-550937 (with English-language translation).
U.S. Appl. No. 12/403,701, filed Mar. 13, 2009, Tsukii, et al.
U.S. Appl. No. 13/355,997, filed Dec. 23, 2011, Tsukii, et al.
Office Action issued Sep. 28, 2012 in Chinese Patent Application No. 201080001877.2 (with English translation).
Pan Yinghua et al., "On the Light Source of ROF System with 60 GHz Millimeter Wave", Optical Device, Nov. 30, 2006.

* cited by examiner

OPTICAL INFORMATION ANALYZER AND OPTICAL INFORMATION ANALYSIS METHOD

TECHNICAL FIELD

The present invention relates to an optical information analyzer and an optical information analysis method. In particular, the present invention relates to an optical information analyzer and an optical information analysis method that emit irradiation light to a sample, which is a measurement target dispersed in a liquid flowing through a flow path, to measure the optical information of the sample.

BACKGROUND ART

An apparatus (a flow cytometer or a cell sorter) has been proposed which makes a liquid containing stained biological particles (minute objects to be measured: samples) flow through a flow path of a flow-path-formed member (flow cell), emits light from an illuminating unit (light emitting unit) to the biological particle, and detects scattered light or fluorescence from the biological particle using a detecting unit (light receiving unit), thereby obtaining the biological information of the biological particle (for example, see Patent Document 1).

In the related art, in the above-mentioned apparatus, a sample flow, which is a stream of the liquid flowing through the flow path of the flow cell, is surrounded by a sheath flow and is adjusted so as to flow in the vicinity of the center of the flow path. The light receiving unit is fixed such that the optical axis and focus of an optical system of the light receiving unit are aligned with the center of flow path in the flow cell on the plane which is substantially orthogonal to the sample flow. In addition, the light emitting unit emits light so as to be focused on the sample flow and receives scattered light or fluorescence from the sample. In this way, it is possible to obtain scattered light or fluorescence with high sensitivity or obtain the optical information of the sample with a small variation. Therefore, it is possible to optimally adjust the position of the optical axis of the light emitting unit with respect to the sample flow while actually emitting light to the sample flow to check the optical information.

CITATION LIST

Patent Document

Patent Document 1: Japanese Patent No. 3891925

DISCLOSURE OF INVENTION

Problems to be Solved by the Invention

However, in the apparatus according to the related art, when the sample flow passes through a position that deviates from the center of the flow path in the flow cell, the optical axis of the optical system of the light receiving unit does not intersect the optical axis of the light emitting unit and the sample flow since the optical axis of the light emitting unit is aligned with the sample flow. Therefore, the light receiving unit is configured so as to receive light within a wide range. As a result, the sensitivity of the detected scattered light or fluorescence is reduced or there is a variation in the obtained optical information of the sample.

In addition, in the apparatus according to the related art, the light receiving unit that receives the side scattered light and/or fluorescence is provided at only one position. Therefore, for example, the sensitivity error of the scattered light or fluorescence occurs due to the direction of the sample when the sample is not a sphere, or the sensitivity error of the scattered light or fluorescence occurs due to the positional deviation of the sample from the center position of the sample flow when the sample does not pass through the center position of the sample flow. As a result, the optical information of the sample with a variation is measured.

The invention has been made in order to solve the above-mentioned problems and an object of the invention is to provide an optical information analyzer and an optical information analysis method capable of improving the sensitivity of side scattered light and/or fluorescence received by a light receiving unit and obtaining the optical information of a sample with a small variation.

Means for Solving the Problem

The following invention is provided in order to solve the above-mentioned problems.

An optical information analyzer according to a first aspect of the invention is an optical information analyzer that emits single-mode light to a sample, which is a measurement target dispersed in a liquid flowing through a flow path, to measure optical information of the sample. The optical information analyzer includes: a light emitting unit that emits the light to the liquid flowing through the flow path; a plurality of scattered light/fluorescence receiving units that receives side scattered light and/or fluorescence generated from the sample by the light emitted from the light emitting unit and detects the side scattered light and/or fluorescence as scattered light/fluorescence signals; and an analyzing unit that measures and analyzes the optical information of the sample on the basis of the scattered light/fluorescence signals detected by each of the scattered light/fluorescence receiving units. The plurality of scattered light/fluorescence receiving units is provided at positions other than a position facing the light emitting unit and the optical axes of all of the scattered light/fluorescence receiving units intersect the optical axis of the light emitting unit.

The single mode is a single transverse mode, and a Gaussian distribution is preferable. However, in the single mode, a portion of the intensity distribution may be substantially uniform or a beam may have an elliptical shape, according to a measurement target. In addition, it is preferable that the intensity of irradiation light be uniform. The scattered light/fluorescence signal is an electric signal converted from the side scattered light and/or fluorescence. In addition, there is a variation in the amount of received light (scattered light/fluorescence signal) during the measurement of the sample. For example, the peak, width, and area of the variation are referred to as optical information.

An optical information analyzer according to a second aspect of the invention is characterized in that, in the optical information analyzer according to the first aspect, at least two of the plurality of scattered light/fluorescence receiving units may be arranged so as to be substantially symmetric with respect to substantially the center position of the plane in the flow path or the optical axis of the light emitting unit.

That is, when the number of scattered light/fluorescence receiving units is three or more, one or more sets of two scattered light/fluorescence receiving units that are symmetric with respect to substantially the center position of the plane in the flow path or the optical axis of the light emitting unit are provided, and the other scattered light/fluorescence receiving units are arranged such that the optical axes thereof pass through substantially the center position of the plane in the flow path substantially orthogonal to the flow direction of the liquid. It is preferable that the number of sets of the scattered light/fluorescence receiving units be as large as possible. For example, when three scattered light/fluorescence receiving units are provided, two of the three scattered light/fluorescence receiving units are arranged so as to face each other with the flow path interposed therebetween and be symmetric with respect to the optical axis of the light receiving unit, and the remaining scattered light/fluorescence receiving unit is arranged such that the optical axis thereof passes through substantially the center position of the plane in the flow path substantially orthogonal to the flow direction of the liquid. When two pairs of four scattered light/fluorescence receiving units are provided, it is more preferable that two scattered light/fluorescence receiving units of each pair face each other with the flow path interposed therebetween and be symmetric with respect to substantially the center position of the plane in the flow path or the optical axis of the light emitting unit.

An optical information analyzer according to a third aspect of the invention is characterized in that, in the optical information analyzer according to the first or second aspect, the analyzing unit may add up the scattered light/fluorescence signals detected by the scattered light/fluorescence receiving units, and measure and analyze the optical information of the sample using the added signal as an independent parameter.

The independent parameters mean factors (here, light signals) used to measure the optical information.

An optical information analyzer according to a fourth aspect of the invention is characterized in that, in the optical information analyzer according to the first or second aspect, the analyzing unit may measure and analyze the optical information of the sample using the scattered light/fluorescence signals detected by the scattered light/fluorescence receiving units as independent parameters.

An optical information analyzer according to a fifth aspect of the invention is characterized in that, in the optical information analyzer according to the fourth aspect, the analyzing unit may correct the scattered light/fluorescence signals detected by the scattered light/fluorescence receiving units on the basis of arrangement coefficients for correcting a signal error due to the arrangement position of the scattered light/fluorescence receiving units.

An optical information analyzer according to a sixth aspect of the invention is characterized in that, the optical information analyzer according to any one of the third to fifth aspects may further include a transmission light receiving unit that receives transmission light, which is the light that is emitted from the light emitting unit and passes through the liquid, and detects the received transmission light as a transmission light signal. The transmission light receiving unit may be arranged such that a light receiving surface substantially orthogonal to the optical axis of the transmission light receiving unit faces the light emitting unit. The analyzing unit may add the transmission light signal detected by the transmission light receiving unit as an independent parameter, and measure and analyze the optical information of the sample using the scattered light/fluorescence signals and the transmission light signal as the independent parameters.

The term "transmission light" means light received by the transmission light receiving unit, such as light that passed through the liquid having the sample dispersed therein, light that passed through the sample, or light that is reflected, scattered, and diffracted by the sample. The term "transmission light signal" means an electric signal converted from the transmission light. Light is received in an arbitrary region receiving the transmission light and the amount of received light (transmission light signal) varies during the measurement of the sample. For example, the peak, width, and area of the variation are referred to as optical information. When the light receiving surface of the transmission light receiving unit faces the light emitting unit, it is preferable that the optical axis of the transmission light receiving unit be substantially parallel to the optical axis of the light emitting unit, the center of the light receiving surface be substantially aligned with the optical axis of the light emitting unit, and the optical axis of the transmission light receiving unit pass through substantially the center position of the plane in the flow path.

An optical information analyzer according to a seventh aspect of the invention is characterized in that, in the optical information analyzer according to the sixth aspect, the transmission light receiving unit may include an optical fiber that transmits the transmission light.

An optical information analyzer according to an eighth aspect of the invention is characterized in that, in the optical information analyzer according to any one of the third to seventh aspects, the analyzing unit may sort the sample on the basis of the measured optical information of the sample.

The sorting of the samples means the classification of samples into a plurality of groups with different shapes or a plurality of different kinds of groups. In addition, the sorting of the samples includes the sorting of the samples S classified into a plurality of groups with different shapes or a plurality of different kinds of groups into, for example, target samples, which are dispensing targets in the downstream process, and non-target samples, which are not dispensing targets in the downstream process.

An optical information analyzer according to a ninth aspect of the invention is characterized in that, in the optical information analyzer according to any one of the fourth to eighth aspects, the analyzing unit may analyze a position where the sample passes on the plane in the flow path on the basis of the measured optical information of the sample.

An optical information analyzer according to a tenth aspect of the invention is characterized in that, in the optical information analyzer according to any one of the first to ninth aspects, the light emitting unit may include an optical fiber that transmits the light.

An optical information analyzer according to an eleventh aspect of the invention is characterized in that, in the optical information analyzer according to any one of the first to tenth aspects, the scattered light/fluorescence receiving unit may include an optical fiber that transmits the side scattered light and/or fluorescence.

An optical information analyzer according to a twelfth aspect of the invention is characterized in that, in the optical information analyzer according to any one of the first to eleventh aspects, an intersection angle between the optical axis of the scattered light/fluorescence receiving unit and the optical axis of the light emitting unit may be in the range of 45 degrees to 90 degrees.

When the optical axes intersect each other, there may be a narrow angle and a wide angle. For example, there may be a narrow angle of 45 degrees and a wide angle of 135 degrees. The intersection angle means the narrow angle.

An optical information analysis method according to a first aspect of the invention is an optical information analysis method of emitting single-mode light to a sample, which is a measurement target dispersed in a liquid flowing through a flow path, to measure optical information of the sample. The method includes: (a) a step of allowing a light emitting unit to emit the light to the liquid flowing through the flow path; (b) a step of allowing a plurality of scattered light/fluorescence receiving units that is provided at positions other than a position facing the light emitting unit and intersects the optical axis of the light emitting unit to receive side scattered light and/or fluorescence generated from the sample by the light emitted in the step (a) and detect the side scattered light and/or fluorescence as scattered light/fluorescence signals; and (c) a step of measuring and analyzing the optical information of the sample on the basis of the scattered light/fluorescence signals detected by each of the scattered light/fluorescence receiving units.

An optical information analysis method according to a second aspect of the invention is characterized in that, in the optical information analysis method according to the first aspect, at least two of the scattered light/fluorescence signals detected by all of the scattered light/fluorescence receiving units in the step (b) may be detected by two scattered light/fluorescence receiving units that are arranged so as to be substantially symmetric with respect to substantially the center position of the plane in the flow path or the optical axis of the light emitting unit.

An optical information analysis method according to a third aspect of the invention is characterized in that, in the optical information analysis method according to the first or second aspect, the step (c) may add up the scattered light/fluorescence signals detected by the scattered light/fluorescence receiving units in the step (b), and measure and analyze the optical information of the sample using the added signal as an independent parameter.

An optical information analysis method according to a fourth aspect of the invention is characterized in that, in the optical information analysis method according to the first or second aspect, the step (c) may measure and analyze the optical information of the sample using the scattered light/fluorescence signals detected by the scattered light/fluorescence receiving units in the step (b) as independent parameters.

An optical information analysis method according to a fifth aspect of the invention is characterized in that, in the optical information analysis method according to the fourth aspect, the step (c) may correct the scattered light/fluorescence signals detected by the scattered light/fluorescence receiving units in the step (b) on the basis of arrangement coefficients for correcting a signal error due to the arrangement position of the scattered light/fluorescence receiving units.

An optical information analysis method according to a sixth aspect of the invention is characterized in that, in the optical information analysis method according to any one of the third to fifth aspects, the step (b) may allow a transmission light receiving unit having a light receiving surface which is substantially orthogonal to the optical axis and faces the light emitting unit to receive transmission light, which is the light that is emitted in the step (a) and passes through the liquid, and detect the received transmission light as a transmission light signal. The step (c) may add the transmission light signal detected by the transmission light receiving unit in the step (b) as an independent parameter, and measure and analyze the optical information of the sample using the scattered light/fluorescence signals and the transmission light signal as the independent parameters.

An optical information analysis method according to a seventh aspect of the invention is characterized in that, in the optical information analysis method according to any one of the third to sixth aspects, the step (c) may sort the sample on the basis of the measured optical information of the sample.

An optical information analysis method according to an eighth aspect of the invention is characterized in that, in the optical information analysis method according to any one of the fourth to seventh aspects, the step (c) may analyze a position where the sample passes on the plane in the flow path on the basis of the measured optical information of the sample.

Effects of the Invention

According to the optical information analyzer and the optical information analysis method of the invention, since a plurality of scattered light/fluorescence receiving units that receives side scattered light and/or fluorescence is provided, a light receiving aperture angle increases. As a result, it is possible to improve the sensitivity of the side scattered light and/or fluorescence received by the scattered light/fluorescence receiving units.

In addition, at least two scattered light/fluorescence receiving units are arranged so as to be symmetric with respect to substantially the center position of the plane in the flow path. Therefore, it is possible to cancel the sensitivity error of the received side scattered light and/or fluorescence due to the direction of the sample when the sample is not a sphere or the positional deviation of the sample from the center of the sample flow and thus obtain the optical information of the sample S with a small variation.

In addition, it is possible to analyze in detail the optical information of the sample on the basis of a plurality of side scattered light and/or fluorescence components received by a plurality of scattered light/fluorescence receiving units and the transmission light received by the transmission light receiving unit.

BEST MODE FOR CARRYING OUT THE INVENTION

Hereinafter, exemplary embodiments of the invention will be described in detail with reference to the accompanying drawings.

Figure 1:
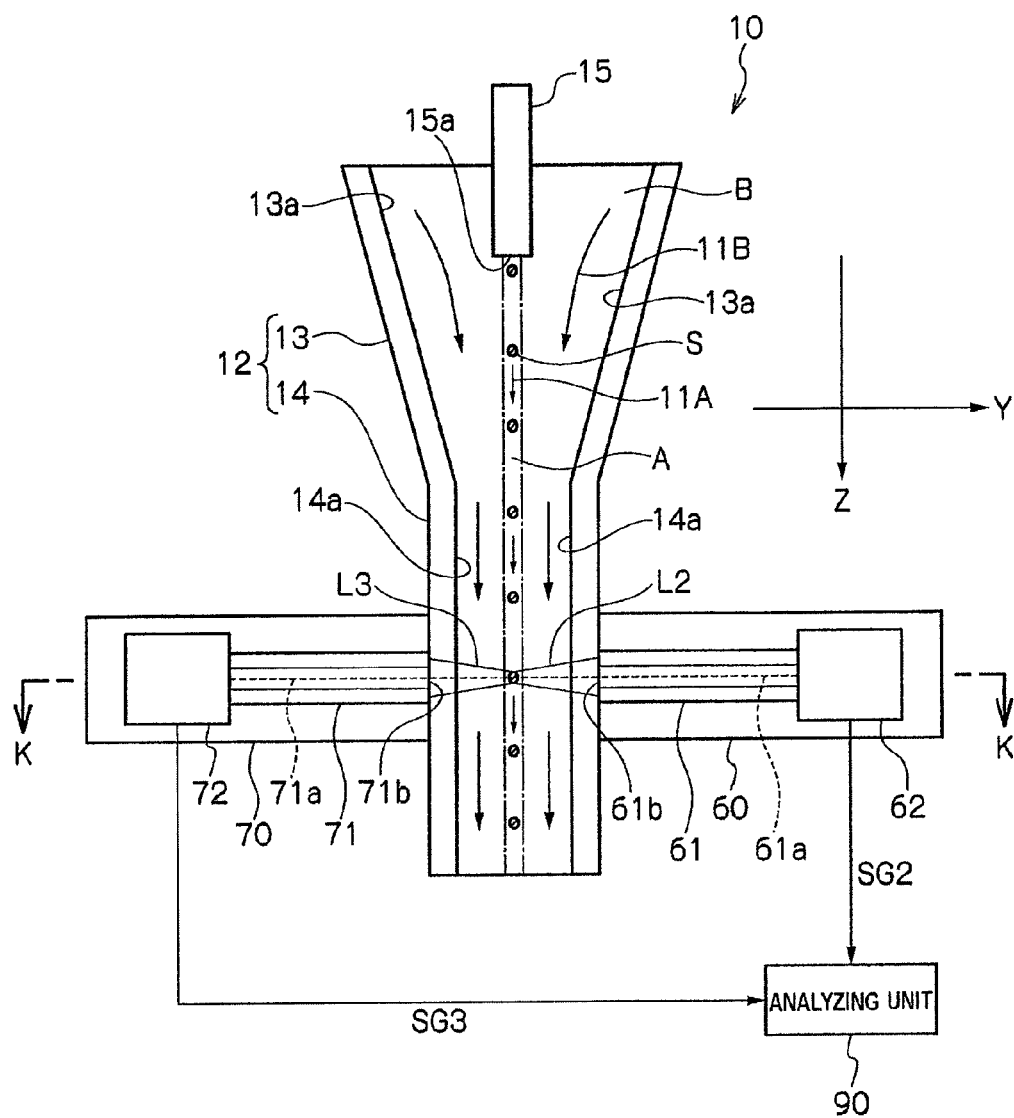
FIG. 1 is a longitudinal cross-sectional view schematically illustrating an optical information analyzer according to an embodiment of the invention.
Figure 2:
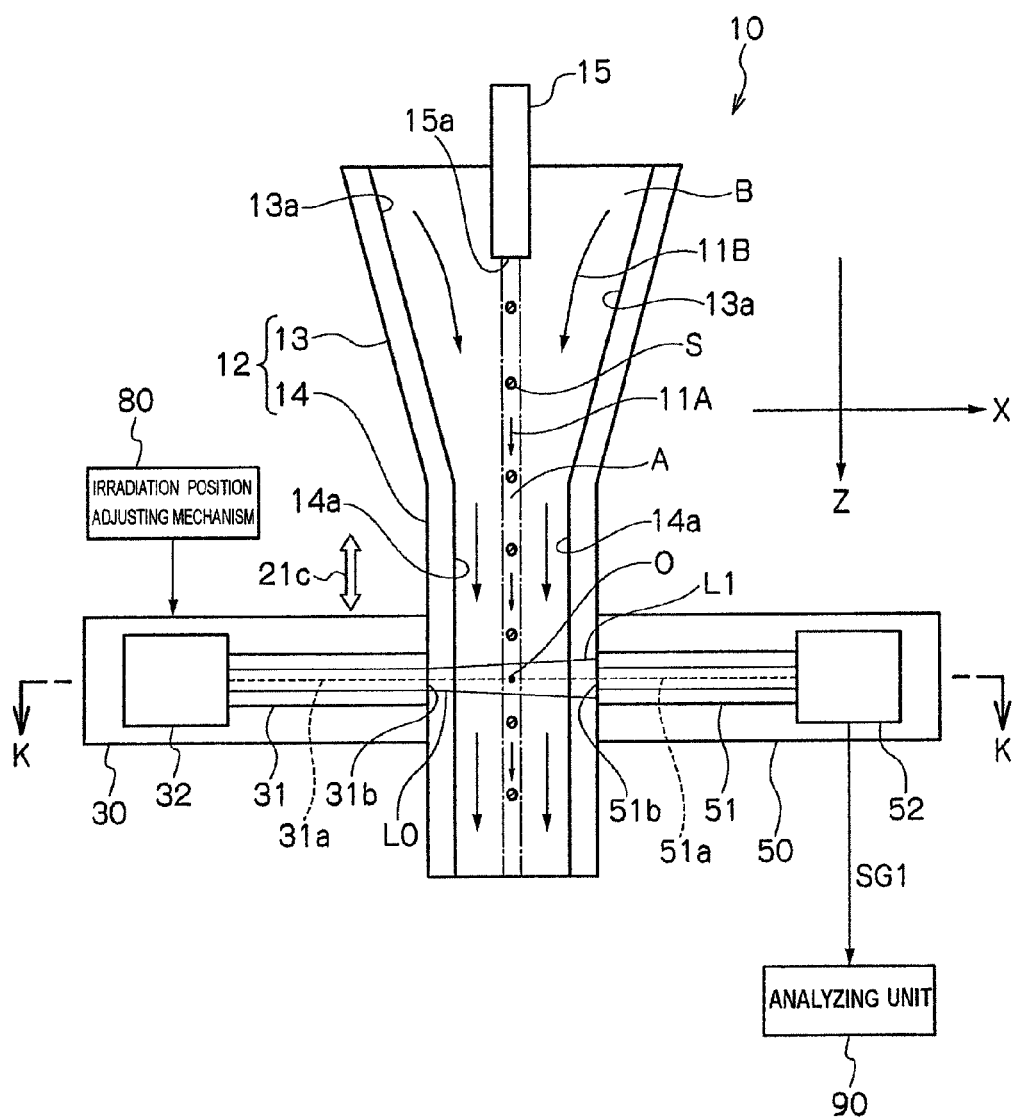
FIG. 2 is a longitudinal cross-sectional view schematically illustrating the optical information analyzer rotated 90 degrees about the Z-axis from the position shown in FIG. 1.
Figure 3:
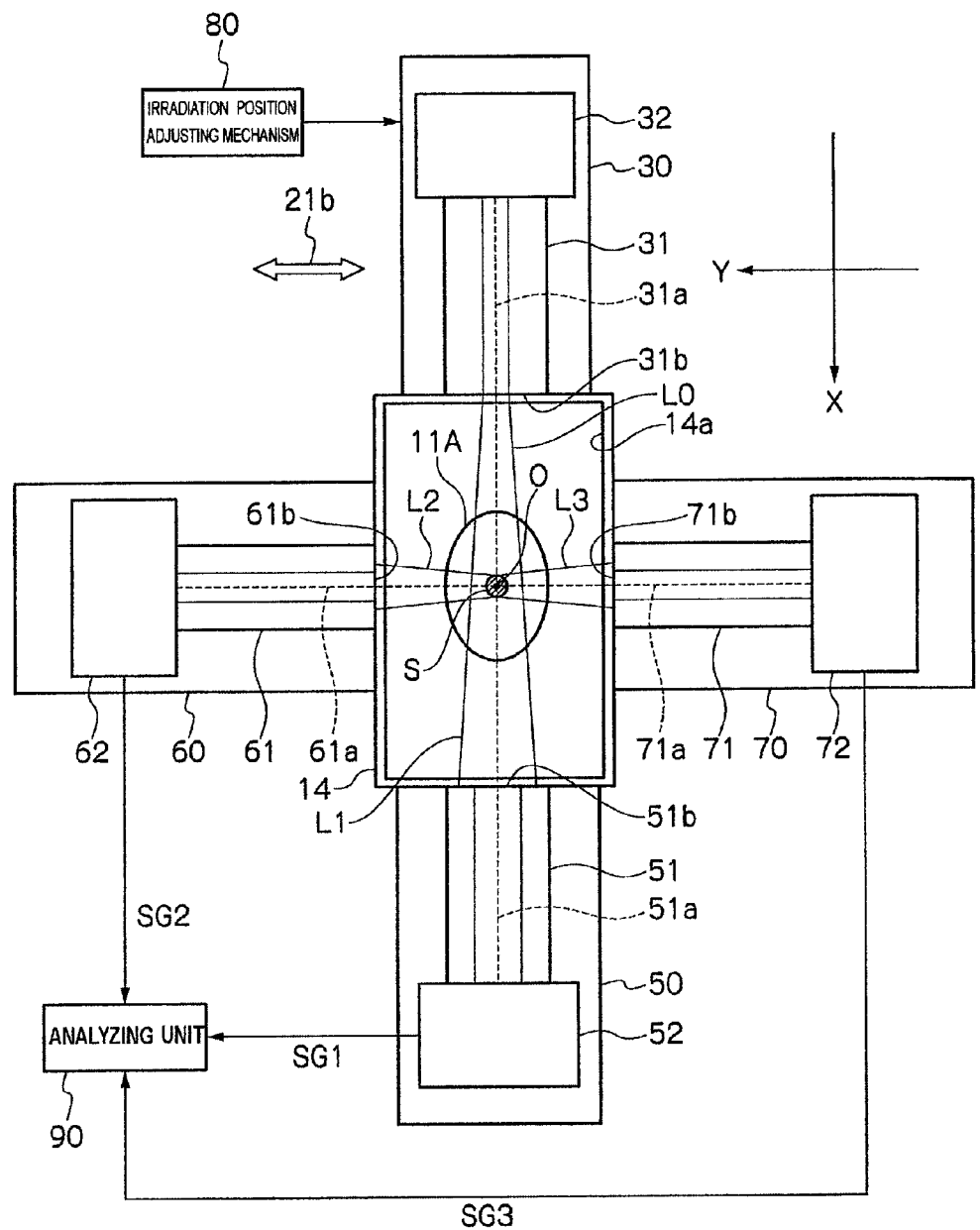
FIG. 3 is a lateral cross-sectional view schematically illustrating the optical information analyzer taken along the line K-K of FIGS. 1 and 2.

FIG. 1 is a longitudinal cross-sectional view schematically illustrating an optical information analyzer according to an embodiment of the invention. FIG. 2 is a longitudinal cross-sectional view schematically illustrating the optical information analyzer that is rotated 90 degrees about the Z-axis from the position shown in FIG. 1. FIG. 3 is a lateral cross-sectional view schematically illustrating the optical information analyzer taken along the line K-K of FIGS. 1 and 2.

As shown in FIGS. 1 to 3, an optical information analyzer 10 according to an embodiment of the invention includes a flow cell 12 including flow paths 13a and 14a through which a liquid A flows, an induction nozzle 15 that introduces the liquid A from a sample storage portion (not shown) to the flow path 13a of the flow cell 12, a light emitting unit 30 that emits single-mode light (excitation light) L0 to a sample S, which is a measurement target dispersed in the liquid A flowing through the flow path 14a of the flow cell 12, a transmission light receiving unit 50 that receives transmission light L1, which is the excitation light passing through the sample S, and detects the transmission light as a transmission light signal SG1, a scattered light/fluorescence receiving unit 60 that receives side scattered light/fluorescence L2 from the sample S and detects the side scattered light/fluorescence L2 as a scattered light/fluorescence signal SG2, a scattered light/fluorescence receiving unit 70 that receives side scattered light/fluorescence L3 from the sample S and detects the side scattered light/fluorescence L3 as a scattered light/fluorescence signal SG3, an irradiation position adjusting mechanism 80 that adjusts the position of the light emitting unit 30, and an analyzing unit 90 that measures the optical information of the sample S on the basis of the transmission light signal SG1 detected by the transmission light receiving unit 50, the scattered light/fluorescence signal SG2 detected by the scattered light/fluorescence receiving unit 60, and the scattered light/fluorescence signal SG3 detected by the scattered light/fluorescence receiving unit 70 and analyzes the sample S on the basis of the optical information. The light emitting unit 30 emits non-focused light L0 to the sample S dispersed in the liquid A flowing through the flow path, and the optical information of the sample S is measured on the basis of the transmission light signal SG1, the scattered light/fluorescence signal SG2, and the scattered light/fluorescence signal SG3 of the sample S detected by the transmission light receiving unit 50 and the scattered light/fluorescence receiving units 60 and 70.

In the specification, the term "transmission light" means light received by the transmission light receiving unit, such as light passing through a liquid having the sample dispersed therein, light passing through the sample, or light that is reflected, scattered, and diffracted by the sample. The term "transmission light signal" means an electric signal converted from the transmission light. The term "scattered light/fluorescence signal" means an electric signal converted from side scattered light and/or fluorescence. Light is received in an arbitrary region receiving the transmission light and the amount of received light (transmission light signal) varies during the measurement of the sample. For example, the peak, width, and area of the variation are referred to as optical information. In addition, for example, the peak, width, and area of a variation in the amount of received side scattered light and/or fluorescence (scattered light/fluorescence signal) during the measurement of the sample are referred to as optical information.

The flow cell 12 includes a tapered portion 13 having a tapered flow path 13a that forms the flow 11B of a sheath liquid B so as to surround the flow of the liquid A having the sample S dispersed therein and forms a straight flow 11A of the liquid A in the Z direction, and a capillary portion 14 having a flow path 14a that maintains the straight flow 11A of the liquid A in the Z direction, is a straight line in the Z direction, and has a rectangular shape in a cross-sectional view orthogonal to the Z direction. The tapered portion 13 and the capillary portion 14 are integrally formed such that the flow path 13a and the flow path 14a are connected to each other. In addition, the flow cell 12 is made of glass or a transparent resin.

In the specification, the sample flow is the flow 11A of the liquid A when the liquid A flows through the flow path 13a and the flow path 14a of the flow cell 12, and the sheath flow is the flow 11B of the sheath liquid B surrounding the sample flow. The direction of the sample flow 11A is the Z direction. A direction that intersects the Z direction and is substantially parallel to the optical axis direction (the direction of the optical axis 51a of an optical fiber 51) of the transmission light receiving unit 50, which will be described below, and the optical axis direction (the direction of the optical axis 31a of an optical fiber 31) of the light emitting unit 30 is the X direction. In addition, a direction orthogonal to the Z direction and the X direction is the Y direction.

The induction nozzle 15 introduces the liquid A from the sample storage unit (not shown) to the flow path 13a of the flow cell 12. The position of the leading end 15a of the induction nozzle 15 is adjusted such that the center of the sample flow 11A passes through substantially the center O of the flow path 14a of the capillary portion 14 on the plane orthogonal to the Z direction. In the specification, the center of the sample flow 11A is the center position in the range in which the sample flow 11A passes on the plane orthogonal to the flow direction (Z direction) of the sample flow 11A.

The light emitting unit 30 includes a semiconductor laser element 32 that emits a laser beam (for example, a beam with a wavelength of 488 nm) with a predetermined wavelength as the light (excitation light) L0 and the optical fiber 31 that propagates the irradiation light L0 so as to be emitted in the vicinity of the flow (sample flow) 11A of the liquid A passing through the flow path 14a. The optical fiber 31 is configured such that the optical axis 31a is substantially aligned with the X direction orthogonal to the Z direction. The light emitting unit 30 includes the optical fiber 31, but any light emitting unit may be used as long as the optical axis is substantially aligned with the X direction orthogonal to the Z direction.

The transmission light receiving unit 50 includes the optical fiber 51 that receives the transmission light L1 from the sample S in the vicinity of the sample flow 11A and a light receiving element 52 that receives the transmission light L1 propagated through the optical fiber 51, detects the received light as the transmission light signal SG1, and transmits the detected transmission light signal SG1 to the analyzing unit 90. For example, a photomultiplier tube or a photodetector may be used as the light receiving element 52.

The optical fiber 51 is provided at a position where it faces the optical fiber 31 with the capillary portion 14 of the flow cell 12 interposed therebetween. The position where the optical fiber 51 faces the optical fiber 31 means a position where a light receiving surface 51b of the optical fiber 51 orthogonal to the optical axis 51a faces an end surface 31b of the optical fiber 31 orthogonal to the optical axis 31a and the optical axis 31a of the optical fiber 31 of the light emitting unit 30 is substantially parallel to the optical axis 51a of the optical fiber 51 of the transmission light receiving unit 50. It is preferable that the irradiation position adjusting mechanism 80 move the position of the optical fiber 31 of the light emitting unit 30 in the Y direction (the direction of an arrow 21b) and the Z direction (the direction of an arrow 21c) to align the optical axis 31a of the optical fiber 31 of the light emitting unit 30 with the optical axis 51a of the optical fiber 51 of the transmission light receiving unit 50. In addition, the optical fiber 51 is fixed to the flow cell 12.

The optical fiber 51 is provided such that the optical axis 51a is aligned substantially in the X direction orthogonal to the Z direction and passes through substantially the center O of the flow path 14a of the capillary portion 14 on the plane substantially orthogonal to the Z direction. The transmission light receiving unit 50 includes the optical fiber 51, but the transmission light receiving unit 50 may be provided such that the optical axis thereof is aligned substantially in the X direction orthogonal to the Z direction and passes through substantially the center O of the flow path 14a of the capillary portion 14 on the plane substantially orthogonal to the Z direction.

The scattered light/fluorescence receiving unit 60 includes an optical fiber 61 that receives the side scattered light and/or fluorescence L2 from the sample in the vicinity of the sample flow 11A and a light receiving element 62 that receives the side scattered light and/or fluorescence L2 propagated through the optical fiber 61, detects the received side scattered light and/or fluorescence L2 as the scattered light/fluorescence signal SG2, and transmits the detected scattered light/fluorescence signal SG2 to the analyzing unit 90. It is preferable that a plurality of light receiving elements 62 be provided so as to receive the side scattered light and/or fluorescence components separated for each wavelength by, for example, optical filters. In this case, the light receiving elements 62 detect different scattered light/fluorescence signals SG2 and a plurality of scattered light/fluorescence signals SG2 detected by the light receiving elements 62 is transmitted to the analyzing unit 90. However, for example, a photomultiplier tube or a photodetector may be used as the light receiving element 62.

The optical fiber 61 is provided such that the optical axis 61a is aligned substantially in the Y direction which is substantially orthogonal to the optical axis 51a of the optical fiber 51 and the optical axis 31a of the optical fiber 31 (that is, substantially orthogonal to the X direction) and is orthogonal to the Z direction and passes through substantially the center O of the flow path 14a of the capillary portion 14 on the plane orthogonal to the Z direction. In addition, the optical fiber 61 is fixed to the flow cell 12. The scattered light/fluorescence receiving unit 60 includes the optical fiber 61, but the scattered light/fluorescence receiving unit 60 may be provided such that the optical axis thereof is aligned substantially in the Y direction and passes through substantially the center O of the flow path 14a of the capillary portion 14 on the plane substantially orthogonal to the Z direction.

The scattered light/fluorescence receiving unit 70 has the same structure as the scattered light/fluorescence receiving unit 60 and includes an optical fiber 71 that receives the side scattered light and/or fluorescence L3 from the sample in the vicinity of the sample flow 11A and a light receiving element 72 that receives the side scattered light and/or fluorescence L3 propagated through the optical fiber 71, detects the received side scattered light and/or fluorescence L3 as the scattered light/fluorescence signal SG3, and transmits the detected scattered light/fluorescence signal SG3 to the analyzing unit 90. It is preferable that a plurality of light receiving elements 72 be provided so as to receive the side scattered light and/or fluorescence components separated for each wavelength by, for example, optical filters. In this case, the light receiving elements 72 detect different scattered light/fluorescence signals SG3 and a plurality of scattered light/fluorescence signals SG3 detected by the light receiving elements 72 is transmitted to the analyzing unit 90. However, for example, a photomultiplier tube or a photodetector may be used as the light receiving element 72.

The scattered light/fluorescence receiving unit 70 is provided at a position where the scattered light/fluorescence receiving unit 70 faces the scattered light/fluorescence receiving unit 60 with the capillary portion 14 interposed therebetween and the scattered light/fluorescence receiving unit 70 and the scattered light/fluorescence receiving unit 60 are symmetric with respect to substantially the center O of the flow path 14a of the capillary portion 14. That is, the optical axis 71a of the optical fiber 71 is aligned with the optical axis 61a of the optical fiber 61, and a light receiving surface 61b of the optical fiber 61 and a light receiving surface 71b of the optical fiber 71 face each other with the capillary portion 14 interposed therebetween and are symmetric with respect to substantially the center O of the flow path 14a of the capillary portion 14.

The scattered light/fluorescence receiving unit 70 includes the optical fiber 71. However, the scattered light/fluorescence receiving unit 70 may be configured such that the optical axis of the scattered light/fluorescence receiving unit 70 is aligned with the optical axis of the scattered light/fluorescence receiving unit 60 and the light receiving surface 61b of the scattered light/fluorescence receiving unit 60 and the light receiving surface 71b of the scattered light/fluorescence receiving unit 70 face each other with the capillary portion 14 interposed therebetween and are symmetric with respect to substantially the center O of the flow path 14a of the capillary portion 14. In addition, the optical fibers 51, 61, and 71 may be provided such that the light receiving surfaces 51b, 61b, and 71b thereof come into direct contact with the sheath flow 11B. When the scattered light/fluorescence receiving units 60 and 70 receive light using lenses, without using the optical fibers 61 and 71, the center of each scattered light/fluorescence receiving region determined by the lens is substantially aligned with the center O of the flow path 14a of the capillary portion 14.

When the number of scattered light/fluorescence receiving units is three or more, one or more sets of two scattered light/fluorescence receiving units that are symmetric with respect to substantially the center position of the plane in the flow path are provided and the other scattered light/fluorescence receiving units are arranged such that the optical axes thereof pass through substantially the center position of the plane in the flow path substantially orthogonal to the flow direction of the liquid. It is preferable that the number of sets of the scattered light/fluorescence receiving units be as large as possible. For example, when three scattered light/fluorescence receiving units are provided, two of the three scattered light/fluorescence receiving units are arranged so as to face each other with the flow path interposed therebetween and be symmetric with respect to substantially the center position of the plane in the flow path, and the remaining scattered light/fluorescence receiving unit is arranged such that the optical axis thereof passes through substantially the center position of the plane in the flow path substantially orthogonal to the flow direction of the liquid. When two pairs of four scattered light/fluorescence receiving units are provided, it is preferable that two scattered light/fluorescence receiving units of each pair face each other with the flow path interposed therebetween and be symmetric with respect to substantially the center position of the plane in the flow path. In addition, it is preferable that the intersection angle between the optical axis of the scattered light/fluorescence receiving unit and the optical axis of the light emitting unit be in the range of 45 degrees to 90 degrees. However, when the optical axes intersect each other, there may be a narrow angle and a wide angle. For example, there may be a narrow angle of 45 degrees and a wide angle of 135 degrees. The intersection angle means the narrow angle.

The analyzing unit 90 measures the optical information of the sample S on the basis of the transmission light signal SG1 detected by the transmission light receiving unit 50, the scattered light/fluorescence signal SG2 detected by the scattered light/fluorescence receiving unit 60, and the scattered light/fluorescence signal SG3 detected by the scattered light/fluorescence receiving unit 70, and analyzes the sample S on the basis of the measured optical information.

The analyzing unit 90 may measure the optical information of the sample S using, for example, a received light signal, which is the sum of the scattered light/fluorescence signal SG2 and the scattered light/fluorescence signal SG3, and the transmission light signal SG1 as independent parameters. When the scattered light/fluorescence signal SG2 and the scattered light/fluorescence signal SG3 are added up to form the received light signal, the sensitivity of the received light signal increases, and an error in the accuracy of the optical information of the sample S due to the direction of the sample S when the sample S is not a sphere or the positional deviation of the sample S from the center of the sample flow 11A is cancelled. Therefore, it is possible to measure the optical information of the sample S with a small variation.

In this embodiment, the scattered light/fluorescence components are guided by the optical fibers 61 and 71 and are than received by the light receiving elements 62 and 72. As a method of adding up the scattered light/fluorescence components, for example, the light receiving element 62 may receive both the scattered light/fluorescence components guided by the optical fibers 61 and 71 and add up the received scattered light/fluorescence components.

Figure 4:
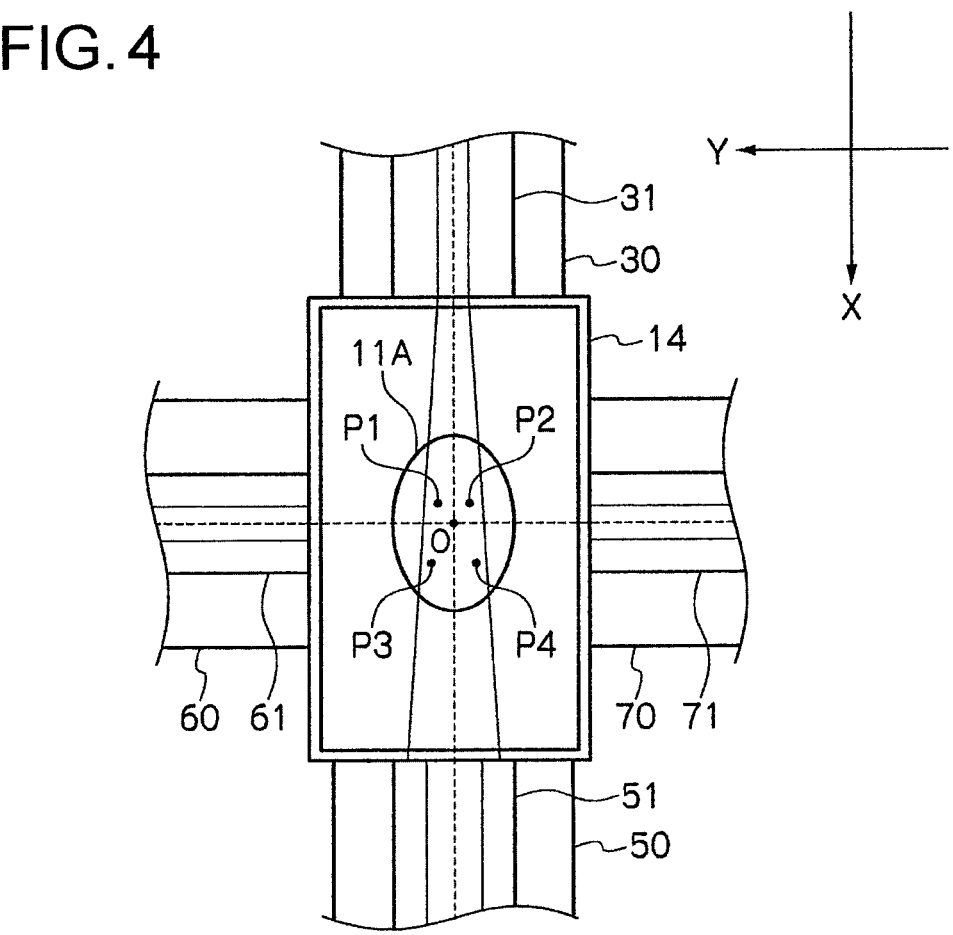
FIG. 4 is a diagram illustrating the positional deviation of a sample S from the center of a sample flow 11A.

FIG. 4 is a diagram illustrating the positional deviation of the sample S from the center of the sample flow 11A, and Table 1 shows an example of the sensitivities of the received light signals according to the positional deviation of the sample S from the center of the sample flow 11A.

flow 11A. The sensitivity value corresponds to the deviation direction and distance from substantially the center O.

For example, Table 1 shows the relationship between the position of the sample S in the sample flow 11A and the sensitivity of the received light signal obtained by multiplying the sensitivity by a sensitivity coefficient according to the positional deviation, assuming that the sensitivity when the position of the sample S deviates from the optical axis 31a of the light emitting unit 30 passing through substantially the center O is 0.5, the sensitivity when the position of the sample S is close to the light receiving surface is 1.5, and the sensitivity when the position of the sample S is away from the light receiving surface is 0.5. However, the above-mentioned sensitivity coefficient may be freely set to an optimal value.

As shown in FIG. 4 and Table 1, the detection sensitivity of the received light signal obtained by adding the scattered light/fluorescence signal SG2 and the scattered light/fluorescence signal SG3 may be more than that of the individual scattered light/fluorescence signal SG2 or the individual scattered light/fluorescence signal SG3. In addition, it is possible to cancel the sensitivity error of the received light signal due to the positional deviation of the sample S from the center of the sample flow and detect the signals. Therefore, it is possible to measure the optical information of the sample S with a small variation. Similarly, it is possible to cancel the sensitivity error of the received light signal due to the direction of

TABLE 1

| Position of sample S | Sensitivity of light signal received by only scattered light/fluorescence receiving unit 60 | Sensitivity of light signal received by only scattered light/fluorescence receiving unit 60 | Sensitivity of light signal received by scattered light/fluorescence receiving units 60 and 70 | Sensitivity of light signal received by transmission light receiving unit 50 |
|---|---|---|---|---|
| Position O (see FIG. 4) | 1 | 1 | 1 + 1 = 2 | 1 |
| Position P1 (see FIG. 4) | 0.5 * 1.5 = 0.75 | 0.5 * 0.5 = 0.25 | 0.5 * 1.5 + 0.5 * 0.5 = 1 | 0.5 * 1.5 = 0.75 |
| Position P2 (see FIG. 4) | 0.5 * 0.5 = 0.25 | 0.5 * 1.5 = 0.75 | 0.5 * 0.5 + 0.5 * 1.5 = 1 | 0.5 * 1.5 = 0.75 |
| Position P3 (see FIG. 4) | 0.5 * 1.5 = 0.75 | 0.5 * 0.5 = 0.25 | 0.5 * 1.5 + 0.5 * 0.5 = 1 | 0.5 * 0.5 = 0.25 |
| Position P4 (see FIG. 4) | 0.5 * 0.5 = 0.25 | 0.5 * 1.5 = 0.75 | 0.5 * 0.5 + 0.5 * 1.5 = 1 | 0.5 * 0.5 = 0.25 |

When the sensitivity of the received light signal when the sample S is disposed substantially at the center of the sample flow 11A (that is, substantially at the center O of the flow path 14a of the capillary portion 14) is 1, the sensitivity of light (the side scattered light and/or fluorescence components L2 and L3 and the transmission light L1) when the position of the sample S deviates from the optical axis 31a of the light emitting unit 30 passing through substantially the center O is less than 1. When the sample S is disposed close to the light receiving surface, the sensitivities of the transmission light L1 and the side scattered light and/or fluorescence components L2 and L3 are greater than 1. When the sample S is away from the light receiving surface, the sensitivities of the transmission light L1 and the side scattered light and/or fluorescence components L2 and L3 are less than 1. As such, each sensitivity value varies depending on the position of the sample the sample S when the sample S is not a sphere and measure the optical information of the sample S with a small variation.

The analyzing unit 90 may measure the optical information of the sample S using, for example, the scattered light/fluorescence signal SG2, the scattered light/fluorescence signal SG3, and the transmission light signal SG1 as independent parameters. As the number of independent parameters increases, it is possible to measure the more detailed optical information of the sample S. The independent parameters mean different factors used to measure the optical information (here, light signals).

The analyzing unit 90 classifies the samples S into a plurality of groups with different shapes (for example, different sizes and shapes) or a plurality of different kinds of groups (for example, different kinds of cells) on the basis of the measured optical information of the samples S. The analyzing unit 90 may sort the samples S classified into a plurality of groups with different shapes or a plurality of different kinds of groups into, for example, target samples, which are dispensing targets in the downstream process, and non-target samples, which are not dispensing targets in the downstream process.

In addition, the analyzing unit 90 analyzes the position where the sample S passes on the plane orthogonal to the Z direction which passes through substantially the center O of the flow path 14a of the capillary portion 14. For example, as shown in FIG. 4 and Table 1, a combination of the sensitivities of the scattered light/fluorescence signal SG2, the scattered light/fluorescence signal SG3, and the transmission light signal SG1 varies depending on the position of the sample S (position 0, position P1, position P2, position P3, and position P4). Therefore, it is possible to analyze the position of the sample S by generating a combination table of the sensitivities of the scattered light/fluorescence signal SG2, the scattered light/fluorescence signal SG3, and the transmission light signal SG1, such as Table 1, in advance using a standard sample and comparing the combination table of the sensitivities with a combination of the sensitivities of the actually detected scattered light/fluorescence signal SG2, scattered light/fluorescence signal SG3, and transmission light signal SG1 of the sample S.

The analyzing unit 90 may correct the sensitivity error of the scattered light/fluorescence signal SG2, the sensitivity error of the scattered light/fluorescence signal SG3, and the sensitivity error of the transmission light signal SG1 due to the deviation of the analyzed position of the sample S from the center of the sample flow (that is, substantially the center O of the flow path 14a of the capillary portion 14) and may perform the process of measuring the optical information of the sample S using the corrected scattered light/fluorescence signal SG2, scattered light/fluorescence signal SG3, and transmission light signal SG1.

The analyzing unit 90 may transmit the analysis result of the sample S to a dispensing unit (not shown) that dispenses the sample S on the basis of the analysis result in the downstream process.

The optical information analyzer 10 according to an embodiment of the invention shown in FIGS. 1 to 3 includes the transmission light receiving unit 50. However, the optical information analyzer 10 may not include the transmission light receiving unit 50. In this case, the analyzing unit 90 performs the process of measuring the optical information of the sample S on the basis of the scattered light/fluorescence signal SG2 and the scattered light/fluorescence signal SG3. In addition, the optical information analyzer 10 may include a front scattered light receiving unit that receives front scattered light, instead of the transmission light receiving unit 50 provided so as to face the light emitting unit 30 with the capillary portion 14 of the flow cell 12 interposed therebetween. In this case, the analyzing unit 90 performs the process of measuring the optical information of the sample S on the basis of the scattered light/fluorescence signal SG2, the scattered light/fluorescence signal SG3, and a front scattered light signal detected by the front scattered light receiving unit.

The optical information analyzer 10 according to an embodiment of the invention shown in FIGS. 1 to 3 includes two scattered light/fluorescence receiving units 60 and 70. However, the optical information analyzer 10 may include three or more scattered light/fluorescence receiving units including the scattered light/fluorescence receiving units 60 and 70, and all of the scattered light/fluorescence receiving units may be configured such that the optical axes thereof pass through substantially the center O of the flow path 14a of the capillary portion 14. In this case, the analyzing unit 90 allocates, to each scattered light/fluorescence receiving unit, arrangement coefficients for correcting an error in the arrangement position or the arrangement of each scattered light/fluorescence receiving unit, that is, for example, the error of the scattered light/fluorescence signals due to the direction of the optical axis of each scattered light/fluorescence receiving unit with respect to the positions of the scattered light/fluorescence receiving units 60 and 70 or the difference between the positions of the light receiving surfaces of the scattered light/fluorescence receiving units, and corrects the scattered light/fluorescence signals detected by each scattered light/fluorescence receiving unit using the allocated arrangement coefficients. In this way, it is possible to measure the optical information of the sample S with a small variation or perform position analysis with high accuracy.

According to the optical information analyzer 10 of an embodiment of the invention, a light receiving aperture angle is increased by providing the scattered light/fluorescence receiving units 60 and 70. As a result, it is possible to increase the sensitivities of the scattered light/fluorescence signal SG2 and the scattered light/fluorescence signal SG3 detected by the scattered light/fluorescence receiving units 60 and 70. In addition, since the scattered light/fluorescence receiving units 60 and 70 are arranged so as to face each other with the capillary portion 14 interposed therebetween and be symmetric with respect to substantially the center O of the flow path 14a, it is possible to cancel an error in the accuracy of the optical information of the sample S due to the direction of the sample S when the sample S is not a sphere or the positional deviation of the sample S from the center of the sample flow and measure the optical information of the sample S with a small variation. In addition, it is possible to analyze in detail the optical information of the sample S on the basis of the scattered light/fluorescence signal SG2, the scattered light/fluorescence signal SG3, and the transmission light signal SG1.

Next, a process of analyzing the optical information of the sample S using the optical information analyzer 10 according to an embodiment of the invention shown in FIGS. 1 to 3 will be described briefly.

Figure 5:
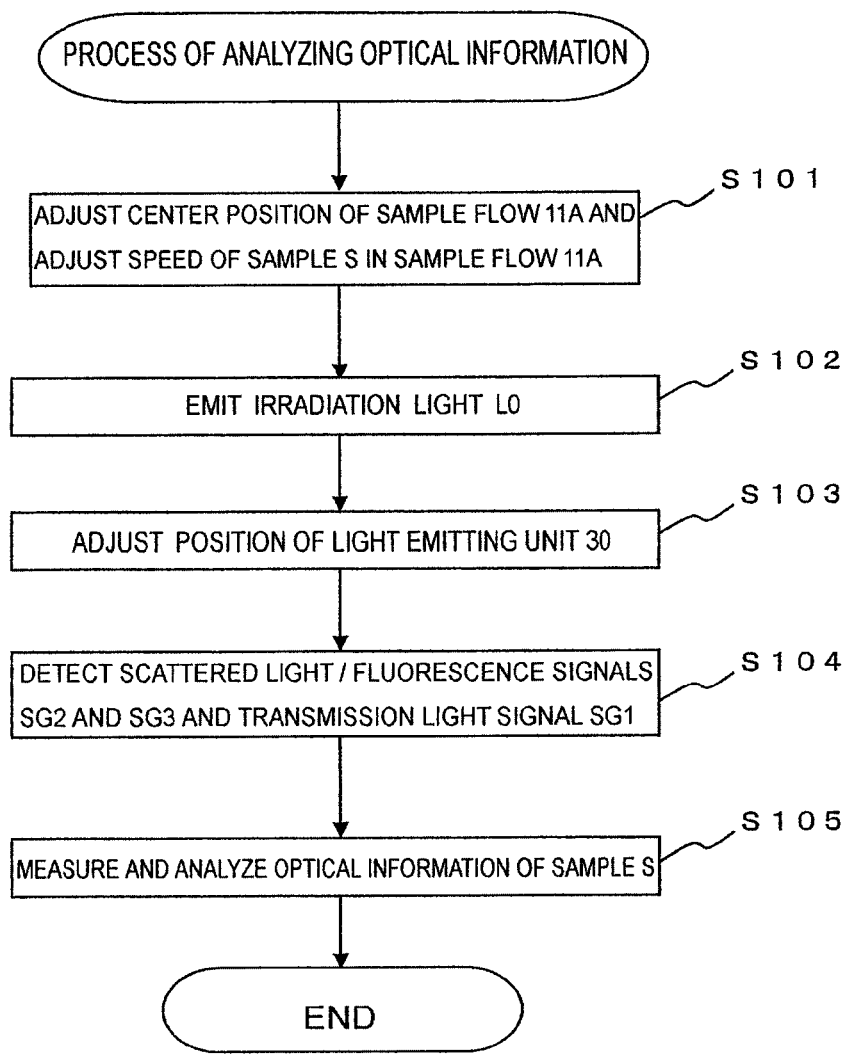
FIG. 5 is a flowchart illustrating a process of analyzing the optical information of the sample S using an optical information analyzer 10 according to an embodiment of the invention shown in FIGS. 1 to 3.

FIG. 5 is a flowchart illustrating the process of analyzing the optical information of the sample S using the optical information analyzer 10 according to an embodiment of the invention shown in FIGS. 1 to 3.

The liquid A is introduced as the sample flow 11A from the sample storage unit (not shown) to the flow path 13a of the flow cell 12 through the induction nozzle 15 and the flow position and the flow rate are adjusted such that the center of the sample flow 11A passes through substantially the center O of the flow path 14a of the capillary portion 14 and the position of the sample S relative to the irradiation light L0 emitted from the light emitting unit 30 is changed at a constant speed.

First, the light emitting unit 30 emits the irradiation light L0 to the capillary portion 14 of the flow cell 12 (Step 1: S101). As shown in FIG. 5, the irradiation position adjusting mechanism 80 moves the position of the optical fiber 31 of the light emitting unit 30 in the Y direction and the Z direction such that the optical axis 31a of the optical fiber 31 of the light emitting unit 30 passes through the center of the sample flow 11A, that is, such that the optical axis 51a of the optical fiber 51 of the transmission light receiving unit 50 fixed to the flow cell 12 passes through substantially the center O of the flow path 14a of the capillary portion 14 and is aligned with the optical axis 31a of the optical fiber 31 of the light emitting unit 30 (Step 2:S102). When the light emitting unit 30 emits light using a lens without using the optical fiber 31, the position of the light emitting unit 30 is adjusted in the X, Y, and Z axes such that the center of an irradiation region determined by the lens is substantially aligned with the center O of the flow path 14a of the capillary portion 14. However, it is not necessary to perform Step 2 each time when the following analysis process (Steps 3 and 4) is performed.

Then, the scattered light/fluorescence receiving units 60 and 70 receive the side scattered light and/or fluorescence components L2 and L3, detect the received side scattered light and/or fluorescence components L2 and L3 as the scattered light/fluorescence signals SG2 and SG3, and transmit the detected scattered light/fluorescence signals SG2 and SG3 to the analyzing unit 90. In addition, the transmission light receiving unit 50 receives the transmission light L1, detects the received transmission light L1 as the transmission light signal SG1, and transmits the detected transmission light signal SG1 to the analyzing unit 90 (Step 3: S103).

Finally, the analyzing unit 90 measures the optical information of the sample S on the basis of the scattered light/fluorescence signals SG2 and SG3 and the transmission light signal SG1 and analyzes the sample S on the basis of the measured optical information (Step 4: S104). In this way, the process of analyzing the optical information of the sample S using the optical information analyzer 10 according to an embodiment of the invention shown in FIGS. 1 to 3 ends. However, a process of dispensing the sample S on the basis of the analysis result obtained in Step 4 may be performed after Step 4.

Specifically, in Step 4, as described in the analyzing unit 90 shown in FIGS. 1 to 3, for example, the process of measuring the optical information of the sample S may be performed using the received light signal, which is the sum of the scattered light/fluorescence signal SG2 and the scattered light/fluorescence signal SG3, and the transmission light signal SG1 as independent parameters. When the scattered light/fluorescence signal SG2 and the scattered light/fluorescence signal SG3 are added up to form the received light signal, the sensitivity of the received light signal increases, and an error in the accuracy of the optical information of the sample S due to the direction of the sample S when the sample S is not a sphere or the positional deviation of the sample S from the center of the sample flow 11A is cancelled. Therefore, it is possible to measure the optical information of the sample S with a small variation.

In Step 4, for example, the process of measuring the optical information of the sample S may be performed using the scattered light/fluorescence signal SG2, the scattered light/fluorescence signal SG3, and the transmission light signal SG1 as independent parameters. As the number of independent parameters increases, it is possible to measure the more detailed optical information of the sample S.

In Step 4, the samples S are classified into a plurality of groups with different shapes (for example, different sizes and shapes) or a plurality of different kinds of groups (for example, different kinds of cells) on the basis of the measured optical information of the samples S. The samples S classified into a plurality of groups with different shapes or a plurality of different kinds of groups may be sorted into, for example, target samples, which are dispensing targets in the downstream process, and non-target samples, which are not dispensing targets in the downstream process.

In Step 4, the position where the sample S passes on the plane orthogonal to the Z direction which passes through substantially the center O of the flow path 14a of the capillary portion 14 is analyzed.

In Step 4, the sensitivity error of the scattered light/fluorescence signal SG2, the sensitivity error of the scattered light/fluorescence signal SG3, and the sensitivity error of the transmission light signal SG1 due to the deviation of the analyzed position of the sample S from the center of the sample flow (that is, substantially the center O of the flow path 14a of the capillary portion 14) may be analyzed, and the process of measuring the optical information of the sample S may be performed using the corrected scattered light/fluorescence signal SG2, scattered light/fluorescence signal SG3, and transmission light signal SG1.

In Step 4, the analysis result of the sample S may be transmitted to a dispensing unit (not shown) that dispenses the sample S on the basis of the analysis result in the downstream process.

The optical information analyzer 10 according to an embodiment of the invention shown in FIGS. 1 to 3 includes the transmission light receiving unit 50. However, the optical information analyzer 10 may not include the transmission light receiving unit 50. In this case, the scattered light/fluorescence signals SG2 and SG3 are detected in Step 3, and the process of measuring the optical information of the sample S is performed in Step 4 on the basis of the scattered light/fluorescence signals SG2 and SG3. In addition, the optical information analyzer 10 may include a front scattered light receiving unit that receives front scattered light, instead of the transmission light receiving unit 50 provided so as to face the light emitting unit 30 with the capillary portion 14 of the flow cell 12 interposed therebetween. In this case, in Step 3, the scattered light/fluorescence signal SG2 and the scattered light/fluorescence signal SG3 are detected and a front scattered light signal is detected by the front scattered light receiving unit. In Step 4, the process of measuring the optical information of the sample S is performed on the basis of the scattered light/fluorescence signal SG2, the scattered light/fluorescence signal SG3, and the front scattered light signal.

The optical information analyzer 10 according to an embodiment of the invention shown in FIGS. 1 to 3 includes two scattered light/fluorescence receiving units 60 and 70. However, the optical information analyzer 10 may include three or more scattered light/fluorescence receiving units including the scattered light/fluorescence receiving units 60 and 70, and all of the scattered light/fluorescence receiving units may be configured such that the optical axes thereof pass through substantially the center O of the flow path 14a of the capillary portion 14. In this case, in Step 4, arrangement coefficients for correcting the error of the scattered light/fluorescence signals due to the arrangement position of each scattered light/fluorescence receiving unit, that is, for example, the error of the scattered light/fluorescence signals due to the direction of the optical axis of each scattered light/fluorescence receiving unit with respect to the positions of the scattered light/fluorescence receiving units 60 and 70 or the difference between the positions of the light receiving surfaces of the scattered light/fluorescence receiving units are allocated to each scattered light/fluorescence receiving unit. Then, the scattered light/fluorescence signals detected by each scattered light/fluorescence receiving unit are corrected using the allocated arrangement coefficients. In this way, it is possible to measure the optical information of the sample S with a small variation.

According to the process of analyzing the optical information of the sample shown in FIG. 5, a light receiving aperture angle is increased by providing the scattered light/fluorescence receiving units 60 and 70. As a result, it is possible to increase the sensitivities of the scattered light/fluorescence signal SG2 and the scattered light/fluorescence signal SG3 detected by the scattered light/fluorescence receiving units 60 and 70. In addition, since the scattered light/fluorescence receiving units 60 and 70 are arranged so as to be symmetric with respect to substantially the center O of the flow path 14a of the capillary portion 14 and it is possible to cancel an error in the accuracy of the optical information of the sample S due to the direction of the sample S when the sample S is not a sphere or the positional deviation of the sample S from the center of the sample flow and measure the optical information of the sample S with a small variation. In addition, it is possible to analyze in detail the optical information of the sample S on the basis of the scattered light/fluorescence signal SG2, the scattered light/fluorescence signal SG3, and the transmission light signal SG1.

The optical information analyzer and the optical information analysis method according to an embodiment of the invention can be applied to various fields in which genes, immune systems, and biopolymers, such as proteins, amino acids, and sugars, need to be examined, analyzed, and assayed, such as an engineering field, an agricultural field including, for example, food, agriculture, and seafood processing, a pharmaceutical field, a medical field including, for example, sanitation, health, immunization, disease, and genetics, and a science field including chemicals and biology.

| Description of Reference Numerals and Signs | |
|---|---|
| 10: | OPTICAL INFORMATION ANALYZER |
| 11A: | SAMPLE FLOW |
| 11B: | SHEATH FLOW |
| 12: | FLOW CELL |
| 13: | TAPERED PORTION |
| 13a, 14a: | FLOW PATH |
| 14: | CAPILLARY PORTION |
| 15: | INDUCTION NOZZLE |
| 30: | LIGHT EMITTING UNIT |
| 31, 51, 61, 71: | OPTICAL FIBER |
| 50: | TRANSMISSION LIGHT RECEIVING UNIT |
| 60, 70: | SCATTERED LIGHT/FLUORESCENCE RECEIVING UNIT |
| 80: | IRRADIATION POSITION ADJUSTING MECHANISM |
| 90: | ANALYZING UNIT |
| S: | SAMPLE |
| L0: | LIGHT |
| L1: | TRANSMISSION LIGHT |
| L2, L3: | SIDE SCATTERED LIGHT AND/OR FLUORESCENCE |
| SG1: | TRANSMISSION LIGHT SIGNAL |
| SG2, SG3: | SCATTERED LIGHT/FLUORESCENCE SIGNAL |

The invention claimed is:

1. An optical information analyzer that emits single-mode light to a sample, which is a measurement target dispersed in a liquid flowing through a flow path, to measure optical information of the sample, the optical information analyzer comprising:
a light emitting unit that emits the single-mode light to the liquid flowing through the flow path;
a plurality of scattered light/fluorescence receiving units that receive side scattered light and/or fluorescence generated from the sample due to the single-mode light emitted from the light emitting unit and detect the side scattered light and/or fluorescence as scattered light/fluorescence signals; and
an analyzing unit that measures and analyzes the optical information of the sample based on the scattered light/fluorescence signals detected by each of the plurality of scattered light/fluorescence receiving units, wherein
the plurality of scattered light/fluorescence receiving units are provided at positions other than a position facing the light emitting unit and optical axes of all of the scattered light/fluorescence receiving units intersect an optical axis of the light emitting unit,
the plurality of scattered light/fluorescence receiving units include a pair of scattered light/fluorescence receiving units arranged to be substantially symmetric with respect to a substantially center position of a plane in the flow path or the optical axis of the light emitting unit, and
the analyzing unit measures a pair of optical information of the sample based on a pair of scattered light/fluorescence signals detected by the pair of scattered light/fluorescence receiving units, and analyzes the sample based on the measured pair of optical information of the sample.

2. The optical information analyzer according to claim 1, wherein the analyzing unit adds up the scattered light/fluorescence signals detected by the scattered light/fluorescence receiving units, and measures and analyzes the optical information of the sample based on the added signal as an independent parameter.

3. The optical information analyzer according to claim 1, wherein the analyzing unit measures and analyzes the optical information of the sample based on the scattered light/fluorescence signals detected by the scattered light/fluorescence receiving units as independent parameters.

4. The optical information analyzer according to claim 3, wherein the analyzing unit corrects the scattered light/fluorescence signals detected by the scattered light/fluorescence receiving units based on arrangement coefficients for correcting a signal error due to the arrangement position of the scattered light/fluorescence receiving units.

5. The optical information analyzer according to any one of claims 2 to 4, further comprising:
a transmission light receiving unit that receives transmission light, which is emitted from the light emitting unit and passes through the liquid, and detects the received transmission light as a transmission light signal, wherein
the transmission light receiving unit is arranged such that a light receiving surface substantially orthogonal to an optical axis of the transmission light receiving unit faces the light emitting unit, and
the analyzing unit adds the transmission light signal detected by the transmission light receiving unit as an independent parameter, and measures and analyzes the optical information of the sample based on the scattered light/fluorescence signals and the transmission light signal as the independent parameters.

6. The optical information analyzer according to claim 5, wherein the transmission light receiving unit includes an optical fiber that propagates the transmission light.

7. The optical information analyzer according to any one of claims 2 to 4, wherein the analyzing unit further sorts the sample based on the measured optical information of the sample.

8. The optical information analyzer according to any one of claims 3 to 4, wherein the analyzing unit analyzes a position where the sample passes on the plane in the flow path based on the measured optical information of the sample.

9. The optical information analyzer according to any one of claims 2, 3, or 4, wherein the light emitting unit includes an optical fiber that transmits the single-mode light.

10. The optical information analyzer according to any one of claims 2, 3, or 4, wherein the scattered light/fluorescence receiving unit includes an optical fiber that transmits the side scattered light and/or fluorescence.

11. The optical information analyzer according to any one of claims 2, 3, or 4, wherein an intersection angle between the optical axis of the scattered light/fluorescence receiving unit and the optical axis of the light emitting unit is in the range from 45 degrees to 90 degrees.

12. The optical information analyzer according to claim 1, wherein the pair of optical information are the same information, in which the pair of scattered light/fluorescence receiving units receive the side scattered light and/or fluorescence that are identical.

13. The optical information analyzer according to claim 1, wherein the pair of scattered light/fluorescence receiving units have the same structure.

14. An optical information analysis method for emitting single-mode light to a sample, which is a measurement target dispersed in a liquid flowing through a flow path, to measure optical information of the sample, the optical information analysis method comprising the steps of:
   (a) allowing a light emitting unit to emit the single-mode light to the liquid flowing through the flow path;
   (b) allowing a plurality of scattered light/fluorescence receiving units, which are provided at positions other than a position facing the light emitting unit and intersect an optical axis of the light emitting unit, to receive side scattered light and/or fluorescence generated from the sample by the single-mode light emitted in the step (a) and to detect the side scattered light and/or fluorescence as scattered light/fluorescence signals; and
   (c) measuring and analyzing the optical information of the sample based on the scattered light/fluorescence signals detected by each of the plurality of scattered light/fluorescence receiving units, wherein
   the plurality of scattered light/fluorescence receiving units include a pair of scattered light/fluorescence receiving units arranged to be substantially symmetric with respect to a substantially center position of a plane in the flow path or the optical axis of the light emitting unit, and
   the measuring and analyzing step includes measuring a pair of optical information of the sample based on a pair of scattered light/fluorescence signals detected by the pair of scattered light/fluorescence receiving units, and analyzing the sample based on the measured pair of optical information of the sample.

15. The optical information analysis method according to claim 14, wherein at least two of the scattered light/fluorescence signals detected by all of the scattered light/fluorescence receiving units in the step (b) are detected by two scattered light/fluorescence receiving units that are arranged so as to be substantially symmetric with respect to a substantially center position of a plane in the flow path or the optical axis of the light emitting unit.

16. The optical information analysis method according to claim 14 or 15, wherein the step (c) adds up the scattered light/fluorescence signals detected by the scattered light/fluorescence receiving units in the step (b), and measures and analyzes the optical information of the sample based on the added signal as an independent parameter.

17. The optical information analysis method according to claim 16, wherein the step (b) allows a transmission light receiving unit having a light receiving surface which is substantially orthogonal to an optical axis of the transmission light receiving unit and faces the light emitting unit to receive transmission light, which is emitted in the step (a) and passes through the liquid, and detect the received transmission light as a transmission light signal, and
   the step (c) adds the transmission light signal detected by the transmission light receiving unit in the step (b) as an independent parameter, and measures and analyzes the optical information of the sample based on the scattered light/fluorescence signals and the transmission light signal as the independent parameters.

18. The optical information analysis method according to claim 14 or 15, wherein the step (c) measures and analyzes the optical information of the sample based on the scattered light/fluorescence signals detected by the scattered light/fluorescence receiving units in the step (b) as independent parameters.

19. The optical information analysis method according to claim 18, wherein the step (c) corrects the scattered light/fluorescence signals detected by the scattered light/fluorescence receiving units in the step (b) based on arrangement coefficients that corrected a signal error due to the arrangement position of the scattered light/fluorescence receiving units.

20. The optical information analysis method according to any one of claim 19, wherein the step (c) analyzes a position where the sample passes on the plane in the flow path based on the measured optical information of the sample.

21. The optical information analysis method according to any one of claims 14 to 15, wherein the step (c) further sorts the sample based on the measured optical information of the sample.

* * * * *